(12) United States Patent
Son

(10) Patent No.: US 10,201,489 B2
(45) Date of Patent: Feb. 12, 2019

(54) METHOD FOR PREVENTING SPONTANEOUS OXIDATION OF ANTIOXIDANT USING APTAMER, APTAMER-BASED CONTROL OF THE RELEASE RATE OF ACTIVE INGREDIENT IN THE HYDROGEL, MATERIAL AND USE THEREOF

(71) Applicant: NEXMOS Co., Ltd, Yongin-si (KR)

(72) Inventor: In-sik Son, Seongnam-si (KR)

(73) Assignee: NEXMOS Co., Ltd, Yongin-si (KR)

( * ) Notice: Subject to any disclaimer, the term of this patent is extended or adjusted under 35 U.S.C. 154(b) by 0 days.

(21) Appl. No.: 15/654,470

(22) Filed: Jul. 19, 2017

(65) Prior Publication Data

US 2017/0326058 A1 Nov. 16, 2017

Related U.S. Application Data

(63) Continuation-in-part of application No. PCT/KR2017/002207, filed on Feb. 28, 2017.

(30) Foreign Application Priority Data

Mar. 4, 2016 (KR) ........................ 10-2016-0026437

(51) Int. Cl.
| | | |
|---|---|---|
| *C12N 15/113* | (2010.01) | |
| *A61K 8/60* | (2006.01) | |
| *A61Q 19/00* | (2006.01) | |
| *A61K 8/04* | (2006.01) | |
| *A61K 8/35* | (2006.01) | |
| *A61K 8/36* | (2006.01) | |
| *A61K 8/65* | (2006.01) | |
| *A61K 8/67* | (2006.01) | |
| *A61K 8/893* | (2006.01) | |
| *A61Q 19/02* | (2006.01) | |
| *A61Q 19/08* | (2006.01) | |
| *C08G 77/18* | (2006.01) | |
| *C12N 15/115* | (2010.01) | |

(52) U.S. Cl.
CPC ............ *A61K 8/606* (2013.01); *A61K 8/042* (2013.01); *A61K 8/35* (2013.01); *A61K 8/36* (2013.01); *A61K 8/65* (2013.01); *A61K 8/676* (2013.01); *A61K 8/893* (2013.01); *A61Q 19/00* (2013.01); *A61Q 19/02* (2013.01); *A61Q 19/08* (2013.01); *C08G 77/18* (2013.01); *C12N 15/115* (2013.01); *A61K 2800/522* (2013.01); *C08G 2210/00* (2013.01); *C12N 2310/16* (2013.01); *C12N 2310/3517* (2013.01)

(58) Field of Classification Search
CPC ....... A61K 8/606; A61K 8/676; C12N 15/115
See application file for complete search history.

(56) References Cited

U.S. PATENT DOCUMENTS

| | | | |
|---|---|---|---|
| 6,235,721 B1 * | 5/2001 | Ghosal ................... | A61K 8/498 424/401 |
| 8,058,415 B2 * | 11/2011 | Lu .......................... | B82Y 15/00 435/6.11 |
| 2007/0112064 A1 | 5/2007 | Lyles | |
| 2013/0196915 A1 | 8/2013 | Wang et al. | |
| 2016/0000901 A1 * | 1/2016 | Blackburn ............... | C12N 7/00 424/194.1 |
| 2016/0017317 A1 * | 1/2016 | Church .................... | C12N 1/38 506/1 |
| 2017/0191060 A1 * | 7/2017 | Jackson ................ | C12N 15/115 |

FOREIGN PATENT DOCUMENTS

KR          101197677      11/2012

OTHER PUBLICATIONS

Nexmos Base Pair Biotechnologies. Inc. and Nexmos, Inc. Creat the first DNA aptamers that inhibit viramin C oxidation, Dec. 28, 2016 , retrieved on May 24, 2018 from www.nexmos.com/view/sub/messageView.php?BOARD_IDX=508&page=1, pp. 1-3 (Year: 2016).*
International Search Report issued, dated Feb. 28, 2017, in response to international Application No. PCT/KR2017/002207 citing WO 20161029139 A1.
WO 20161029139 A1 citted in International Search Report dated Feb. 28, 2017.
Barrita, Jose Luis Silencio etc., 'Antioxidant role of ascorbic acid and his protective effects on chronic diseases', Oxidative Stress and Chronic Degenerative Diseases—A Role for Antioxidants, Edited by Jose A. Morales-Gonzalez, Intech, 2013, pp. 449-484, ISBN:978-953-51-1123-8.

* cited by examiner

Primary Examiner — Brian Whiteman

(57) ABSTRACT

The present disclosure relates to a method for preventing spontaneous oxidation of an antioxidant, material thereof and uses thereof. More particularly, the present disclosure relates to a method for preventing oxidation of an antioxidant using aptamer specifically binding to its target antioxidant and aptamer-based control of the release rate of active ingredient in the hydrogel. Aptamer having such activity can have versatile applications such as cosmeceuticals and health beverages. As an example, we provide in the present disclosure the establishing method of aptamer targeting for Vitamin C and verification of its prevention of spontaneous oxidation of Vitamin C. We also provide the detailed method for trapping such aptamer-active ingredient complex in the hydrogel. It is expected that an aptamer-trapped hydrogel of the present disclosure has functions of controlling a release rate of the active ingredient through the aptamer-based sensing of specific substance released from the skin according to the skin conditions.

2 Claims, 15 Drawing Sheets
Specification includes a Sequence Listing.

METHOD FOR PREVENTING SPONTANEOUS OXIDATION OF ANTIOXIDANT USING APTAMER, APTAMER-BASED CONTROL OF THE RELEASE RATE OF ACTIVE INGREDIENT IN THE HYDROGEL, MATERIAL AND USE THEREOF

CROSS-REFERENCE TO RELATED APPLICATIONS

This application is the continuation-in-part application of copending PCT application Ser. No. PCT/KR2017/002207 filed on Feb. 28, 2017, that claims priority to Korean Patent Application No. 10-2016-0026437 filed on Mar. 4, 2016, with the Korean Intellectual Property Office, the disclosure of which is incorporated herein in its entirety by reference.

TECHNICAL FIELD

The present disclosure relates to a method for preventing the oxidation of an antioxidant using nucleotide aptamer, its material, and its use.

BACKGROUND

There are many reasons for promoting aging, but reactive oxygen species (ROS) is considered to be one of the major causes. This ROS is indispensably produced in energy metabolism, immune response, etc., and is generated by inevitable stimulus caused by external harmful environment. ROS is highly reactive to cause DNA degeneration, induction of excessive signal transmission, protein denaturation, etc. in the body, resulting in a series of reactions accumulating adverse health effects.

However, in these harmful conditions, homeostasis have been elaborately maintained by external antioxidants (uric acid, vitamin C, vitamin E, etc.) or endogenous antioxidant enzymes (glutathione peroxidase, superoxide dismutase, catalase, etc.) which present in the body. However, the aging of the antioxidant system due to the endogenous aging and the accumulation of ROS by the continuous and noxious stimuli may break this balance, promoting aging, causing various diseases such as skin diseases, skin cancer, arteriosclerosis, and thrombosis (Laure Rittie et al., Aging Research Reviews, 1, 705-720, 2002; Cutler R G, Annals of the New York Academy of Sciences, 1055, 93-135, 2005).

Accordingly, there is a growing interest in antioxidants that inhibit the formation of reactive oxygen species (ROS) or removing ROS. Antioxidants can be divided into those that are naturally present in the body (endogenous antioxidant) and those that are administered externally (exogenous antioxidant).

Antioxidants that are naturally present in the body include enzymes such as superoxide dismutase (SOD), glutathione, peroxidase, and catalase. Externally administered antioxidants include phytochemicals such as kaempferol, catechin, and genistein; vitamin E, vitamin C, and beta carotene; and minerals such as selenium.

Vitamin C (L-ascorbic acid, ascorbate) is essential for humans and other animals, and is important for collagen synthesis, etc., and is a cofactor for at least eight enzymes. Therefore, vitamin C deficiency causes diseases such as scurvy. In animals, vitamin C is an important factor to prevent wound healing and capillary hemorrhage, and is a critical antioxidant in the body along with vitamin A, vitamin E, and others.

Cells are attacked by free radicals, oxygen free radicals, and etc. caused by ultraviolet A (UVA) and ultraviolet B (UVB) irradiated from, sunlight, pollutants, stress, smoking, drinking, and fatty foods. If the proper protection from these materials is not achieved, the cells will age or die. In the case of skin, the production of materials such as collagen and elastin is reduced or denatured by these materials, causing the skin to lose its elasticity and resulting in wrinkles. In order to prevent this, it is known that it is important to prevent aging of the skin by applying a preparation containing antioxidants such as vitamins A, C, and E to the skin and absorbing it into the skin by preventing oxidation from the harmful environmental factors. However, vitamin C (L-ascorbic acid) is easily oxidized in the air and by sunlight, and thus its antioxidant effect disappears. Therefore, there is a problem in manufacturing various formulations having a long storage period.

Meanwhile, hydrogel refers to a material having a high-water content (90% or more) made of a hydrophilic polymer. There are many kinds of materials such as natural materials (collagen, etc.) and synthesized materials (silicone hydrogels, polyacrylamides, polymacon).

It is highly demanded that the active ingredient is promptly transferred into the skin within a short time of 20 minutes to 30 minutes after the hydrogel is applied to the skin. To do so, the active ingredient in the hydrogel must be promptly and uniformly transferred to the skin.

While the state of the hydrogel is maintained, effective cosmetic ingredients in the gel are limited in sustaining a satisfactory amount and speed to be delivered from the hydrogel to the skin is also very limited. In addition, the water and the active ingredient in the hydrogel are evaporated as time passes so that it is not possible to take its advantages. Therefore, even if the hydrogel has unique adhesiveness and wettability, the limit of the effective ingredient contained in the hydrogel as well as the limit of the delivery speed of the effective cosmetic ingredient to the skin results in restriction of the skin penetration efficiency of the hydrogel mask pack, which is disclosed in Korean Patent No.: 10-1197677.

SUMMARY

The present disclosure has been made in view of the above needs, and an object of the present disclosure is to provide a method for preventing spontaneous oxidation of an antioxidant using aptamer.

Another object of the present disclosure is to provide material preventing spontaneous oxidation of antioxidant.

Still another object of the present invention is to provide a method for functionalized hydrogel which contains aptamer preventing oxidation of an antioxidant and has a function of controlling the release rate and composition of active cosmeceutical ingredient according to the amount of a specific substance released from the skin.

In order to achieve the objects as described above, the present disclosure provides a method for establishing aptamer which prevents spontaneous oxidation of an antioxidant.

In one embodiment of the present disclosure, the antioxidant is preferably, but not limited to, a material selected from the group consisting of vitamin C, vitamin A, retinol, vitamin E, astaxanthin, resveratrol, polyphenol, coenzyme Q10, peptides, and oils.

In one embodiment of the present disclosure, an example of the aptamer is preferably a single-strand DNA nucleotide whose sequence is shown in SEQ ID NO: 1. However, in addition to such aptamer, all the aptamers which achieve the desired effect of the present disclosure and have other sequences as demonstrated by the examples of the present disclosure are included in the scope of protection of the present disclosure.

In another embodiment of the present disclosure, when the antioxidant is vitamin C, the aptamer preferably but not limited to inhibits the oxidation of the second and third OH groups of the lactone ring of vitamin C.

Further, the present disclosure provides an aptamer for preventing oxidation of the antioxidant.

Further, the present disclosure also provides a method for producing an aptamer-trapped hydrogel, including the steps of a) binding an amine group to an aptamer of the present disclosure, b) silanizing hydroxyl group of the hydrogel monomer with 3-glycidoxypropyltrimethoxysilane (3-GPTMS) and then binding the aptamer-bound amine group to the epoxy group, and c) polymerizing the hydrogel monomer.

In one embodiment of the present disclosure, a method includes the steps of binding biotin to the aptamer-bound amine group of the step a), reacting them with a particle having streptavidin, and then mixing the particles having the aptamer with the hydrogel monomer during the hydrogel polymerization.

In another embodiment of the present disclosure, a method preferably, but not limited to, chemically binds an amine group or a carboxyl group attached to the aptamer to the hydroxyl group of the hydrogel.

Further, the present disclosure provides an aptamer trapped hydrogel produced by the method of the present disclosure.

In one embodiment of the present disclosure, the hydrogel is such that the aptamer is attached to a surface of hydrogel and a specific ingredient is attached to an end of the aptamer. The specific ingredient is preferably, but not limited to, a component having skin aging resistance, wrinkle removal, whitening, and moisturizing effect.

The specific ingredient of the present disclosure may be any raw material used in cosmetics, regardless of the kind of extracts or active ingredients.

Examples thereof may include various extracts such as, for whitening, a green tea extract, a licorice extract, a mulberry extract, a mulberry root extract, a golden extract, a pueraria extract, a red ginseng extract, for preventing aging, an apricot extract, an oil extract, an orange extract, a lemon extract, a bamboo extract, a guava extract, a rosemary extract, a cornus officinalis extract, a lingshi mushroom extract, a ginkgo extract, a gleditschia australis thorn extract, a paeonia lactiflora root extract, for moisturizing, a quince extract, a white lotus flower extract, a paprika extract, an aloe extract, a cylindrica extract, a seaweed extract, for anti-oxidation, a carrot extract, a soybean extract, a grapefruit seed extract, a grape seed extract, a portulaca oleracea extract, for improving wrinkles, caviar, pomegranate, a ginseng extract, for skin reproduction, a peach extract, a cnidium officinale MAKINO extract, for treating atopy, a centella asiatica extract, a chamomile extract, an adriatic root extract, a sophora flavescens extract, an angelica extract, for treating acne, a peppermint extract, a saururus chinensis extract, a heartleaf houttuynia extract, a peony extract, for anti-inflammatory or anti-bacteria, pyrolignous liquor, a dandelion extract, a calendula extract, a phellodendron amurense extract, a trifoliate orange extract, a golden extract, a fennel extract, a compuri extract, for shrinking pores, a castanea crenata shell extract, a green tea extract, for moisture, glycerin, panthenol, hyaluronic acid, ceramide, beta-glucan, for whitening, albutin, vitamin C, whitense, retinol, astaxanthin, resveratinol, polyphenol, for elasticity, elastin, collagen, coenzyme Q10, effectin, EGF, for anti-infective anti-bacterial agent, propolis, allantoin, phytostan, infra acid, antioxidant vitamin E (natural tocopherol) ROE (a rosemary oil extract), a grapefruit seed extract.

Further, the present disclosure provides a cosmetic composition including the aptamer-trapped hydrogel of the present disclosure.

Further, the present disclosure provides a method for controlling the release of the skin active material according to the amount of the target material released from the skin, including the steps of applying an aptamer-trapped hydrogel of the present disclosure to the skin to cause the aptamer binding to an ingredient from the hydrogel, so as to penetrate into the skin, binding the ingredient-aptamer complex to the target substances from the skin, and releasing an active ingredient from hydrogel.

In one embodiment of the present disclosure, the target substance forming the skin is preferably, but not limited to, ATP whose levels are changed according to the skin condition. Because aptamers can effectively stabilize antioxidants presented in the present disclosure including vitamin C, peptide, and retinol, by preventing its spontaneous oxidation, it is expected that its cosmeceutical effects for skin whitening and wrinkle improvements could be improved when they are slowly released from the hydrogels.

The use of cosmetic raw material/materials using the aptamer-hydrogel of the present disclosure is summarized as follows.

As widely known, materials used as the main ingredients of functional cosmetics such as vitamin C, peptide, and retinol are very unstable. When the materials are exposed to air and light, they are easily oxidized and lose their antioxidant function quickly. These materials are captured by the aptamer to inhibit the materials to bind to the oxygen (oxidation), thereby giving the role of sustaining the materials as stable as possible (continuous function).

The release rate of the active cosmeceutical ingredients is controlled by aptamers. Since most hydrogels have non-compact structure, the permeability is high for many kinds of materials so that the materials contained therein are easily released. It has been experimentally proven that when aptamer which reacts with specific active ingredient is included in the hydrogel, the release rate of the materials can be controlled by controlling the binding force of the aptamer to the materials.

Aptamer can regulate the release rate of the active ingredients according to the amount of the specific substance released from the skin. This technique, called Aptasensing, is a method that can be used for various purposes such as cosmetics and therapy by releasing the necessary materials to the skin according to the condition of the skin after detecting the various states of the skin.

There is an implementable system that detects ATP released at a different concentration depending on the temperature of the skin, or detects, e.g., cytokines, by the aptamer, then the active ingredients are released according to the skin condition. Thus, it allows an appropriate amount of various active ingredients to be released by sensing the skin conditions so as to be designed to control the duration time or reduce unnecessary overload to the skin.

A three-dimensional structure of aptamers such as single strand DNA or RNA confers great flexibility and specificity toward its target molecule. Even though it is similar to an antigen-antibody reaction, its size is much smaller, and its activity can be controlled by various methods. Thus, it has the advantages of easy production and storage as compared to antibodies. Further, the aptamer may be synthesized to bind to a chemical substance (vitamin) having a very small size, unlike an antibody. Since it is produced by chemical synthesis, it is easy to maintain its effect constantly.

Vitamin C is a water-soluble six-carbon compound, which includes a reduced form in which C-3 and C-4 (3- and 4-) are formed in dihydroxy and semidehydroascorbic acid and dehydroascorbic acid in which those carbons are oxidized respectively.

The reduced state of vitamin C is maintained through the hydrogen bonding of the hydroxyl group of vitamin C and the base constituting the aptamer (RNA or DNA) of the present disclosure (See FIG. 1).

Vitamin C, which is in a reduced state in combination with the aptamer of the present disclosure, can be used for nutritional supplements or cosmetic compositions of various formulations of hydrogel-type or cream-type, including, e.g., collagen, elastin, hyaluronic acid, and peptides.

The present disclosure also includes a method for slowly releasing vitamin C according to various conditions of the skin through aptamer (aptasensing) which differently reacts depending on the state of the skin or external stimuli (for example, ultraviolet rays, skin temperature, and acidity). Such examples include a method that the bound vitamin C is released when the structure of the aptamer is changed depending on the irradiation ultraviolet on the skin, and that vitamin C is released when the amount of ATP is changed depending on the change of the skin temperature or acidity.

As can be seen from the present disclosure, the aptamer of the present disclosure has a preventive effect of spontaneous oxidation of antioxidants such as vitamin C, which dramatically improve its capability so as to maintain its active antioxidant functions. When this aptamer-antioxidant complex is trapped in the hydrogels, it is expected that aptamer can maintain the functions of antioxidants much longer and make a sustainable antioxidant effect for a longer period. In addition, an aptamer can control the release rate of the active cosmeceutical ingredients such as Vitamin C according to the skin conditions by sensing the substances released from the skin whose concentrations reflect skin conditions including pH and temperature.

DETAILED DESCRIPTION

Hereinafter, the present disclosure will be described in detail with reference to non-limiting Examples. The following Examples are intended to illustrate the present disclosure, and the scope of the present disclosure is not to be construed as being limited to the following Examples.

Example 1: Construction of a Group of Aptamers Binding to Reduced Vitamin C

The systematic evolution of ligands by exponential enrichment (SELEX) was carried out under the following conditions, finding the aptamer which selectively binds to the reduced ascorbic acid from DNA aptamer library including $10^{13}$ of aptamers. To proceed with SELEX while the reduced state of ascorbic acid was maintained, glutathione was added while maintaining a pH of about 5.5.

Under these conditions, more than 99% of the vitamin C was maintained in the reduced L-ascorbic acid state, rather than the oxidized dehydroascorbic acid (DHA). Under the above reaction conditions, SELEX was carried out, and the entire selected aptamers were subjected to Next Generation Sequencing. As an analysis result, aptamers composed of 3000 or more of secondary structure group were obtained.

Example 2: Quantitative Analysis of Anti-Oxidation of Vitamin C by Aptamer

Twenty individual aptamers were selected according to the type of the secondary structure, and the experiment regarding prevention of oxidation of vitamin C was carried out. After the aptamer dissolved in the annealing buffer was heated to 95° C., the secondary structure of the aptamer was formed as the temperature was gradually lowered to room temperature. Then, the mixture was mixed and reacted with the reduced L-ascorbic acid for 30 minutes so as to allow the mixture to bind to the L-ascorbic acid. Then, hydrogen peroxide solution was added to provide the oxidation condition. Oxidation of L-ascorbic acid was measured by adding OPDA (o-phenylenediamine) as a fluorescent dye. The level of DHA production can be quantitatively analyzed by measuring the amount of fluorescence from DHA-OPDA produced by the reaction of DHA, an oxide of L-ascorbic acid, with OPDA. Under the above conditions, the amount of fluorescence of DHA-OPDA was measured every 34 seconds for 25 minutes.

Figure 1:
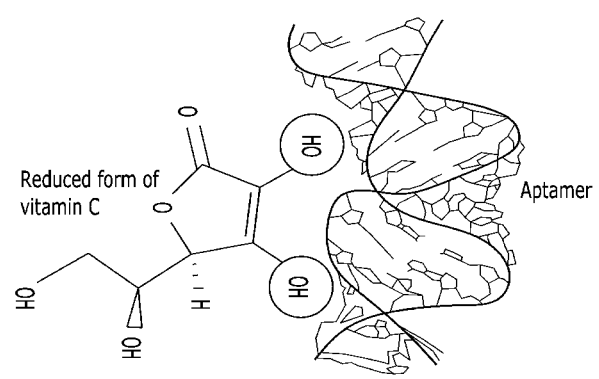
FIG. 1 shows the reduction state of vitamin C through the hydrogen bonding of the hydroxyl group of vitamin C with bases constituted in an aptamer (RNA or DNA)
Figure 2:
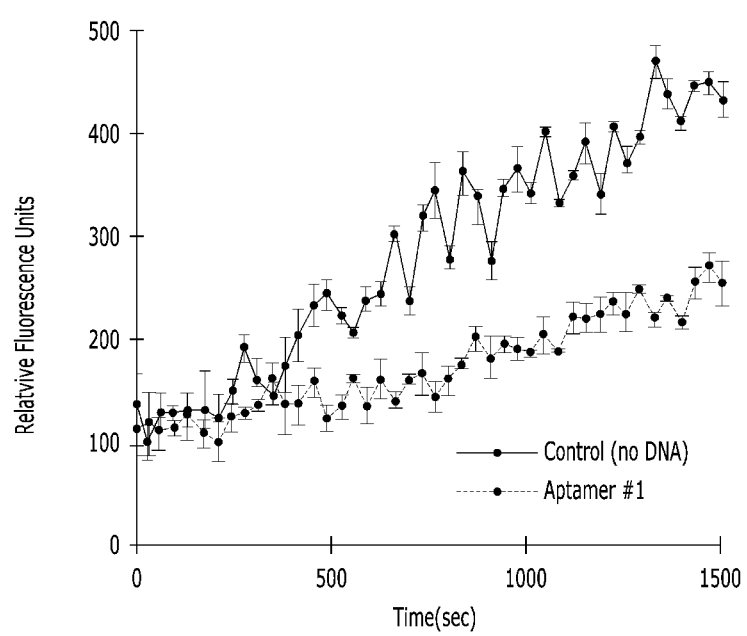
FIGS. 2 to 4 show that the three aptamers of the present disclosure prevent oxidation of vitamin C by hydrogen peroxide, more details
Figure 3:
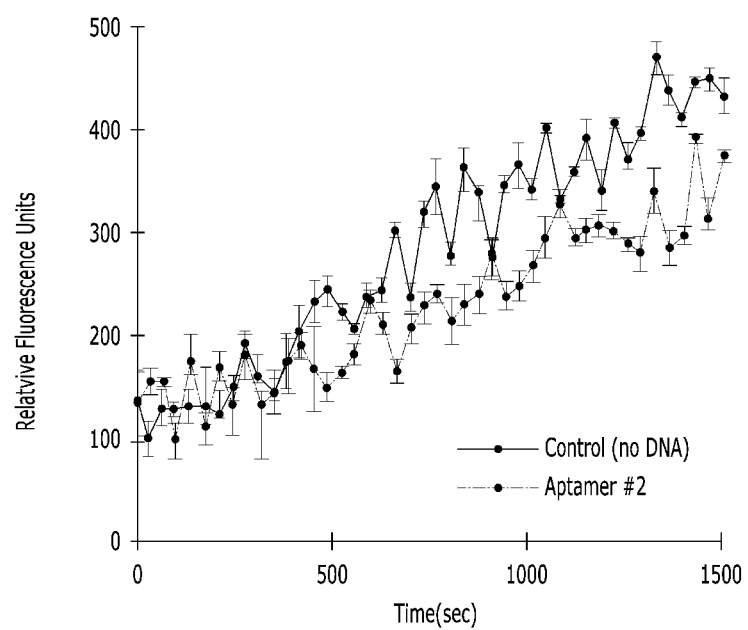
Figure 4:
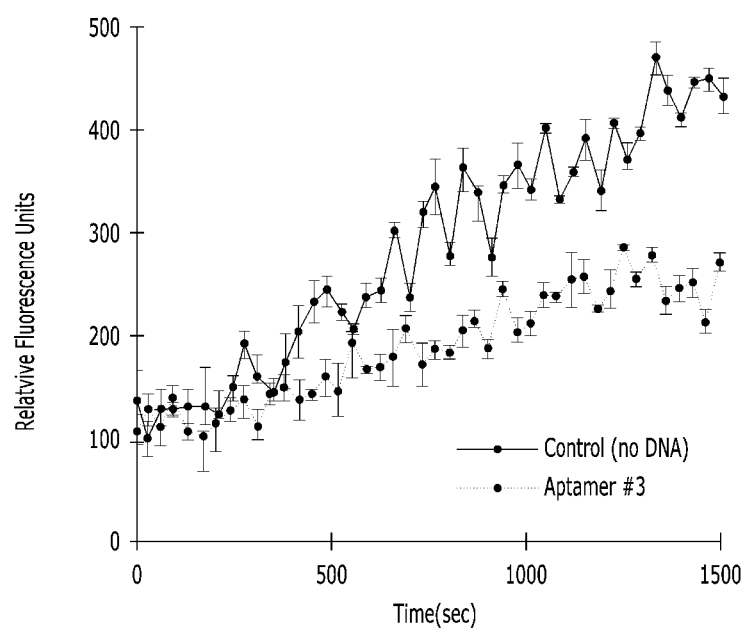
Figure 5:
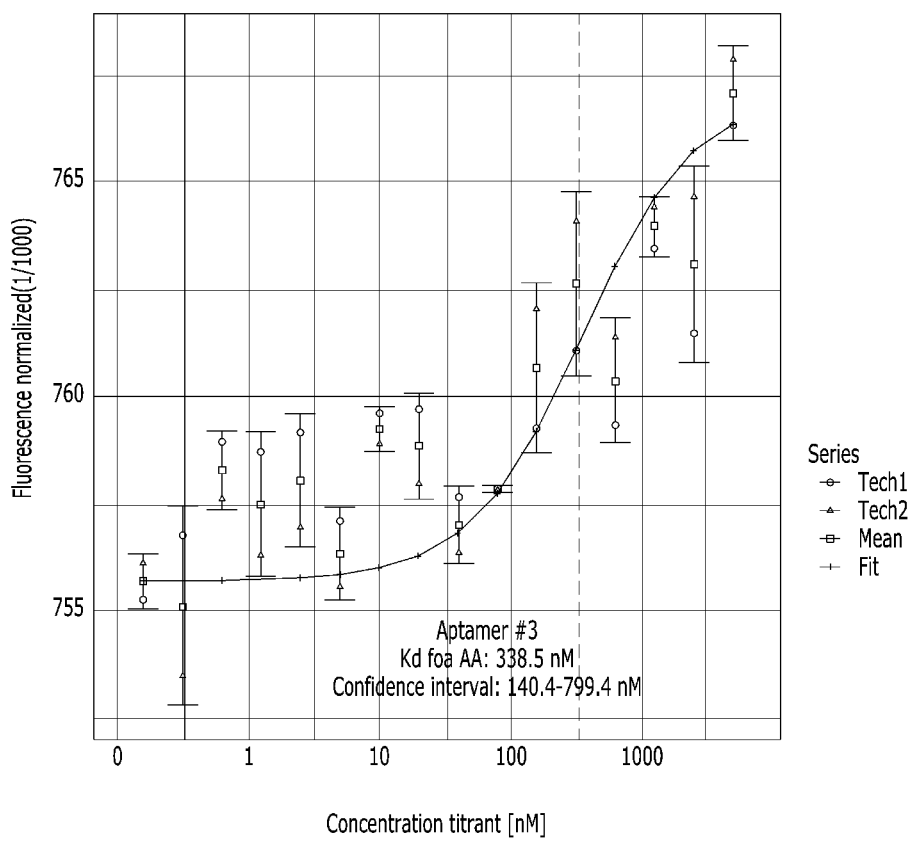
FIGS. 5 to 10 are graphs showing dissociation constants (KD) for AA (ascorbic acid) and DHA (dehydroascorbic acid) of an aptamer of the present disclosure.
Figure 6:
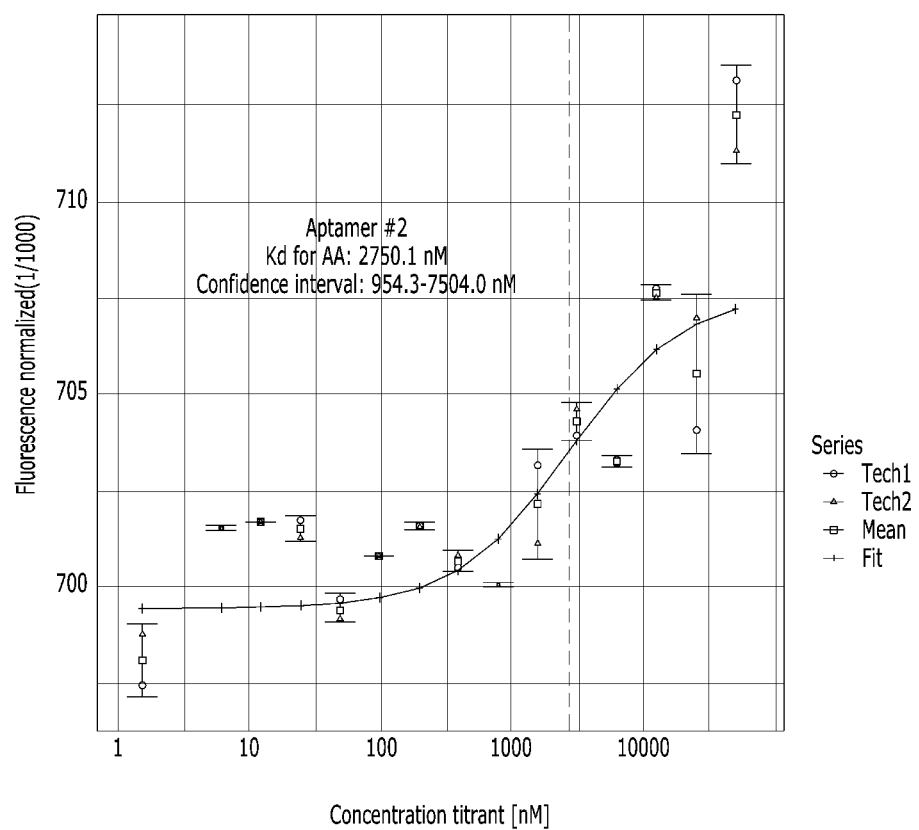
Figure 7:
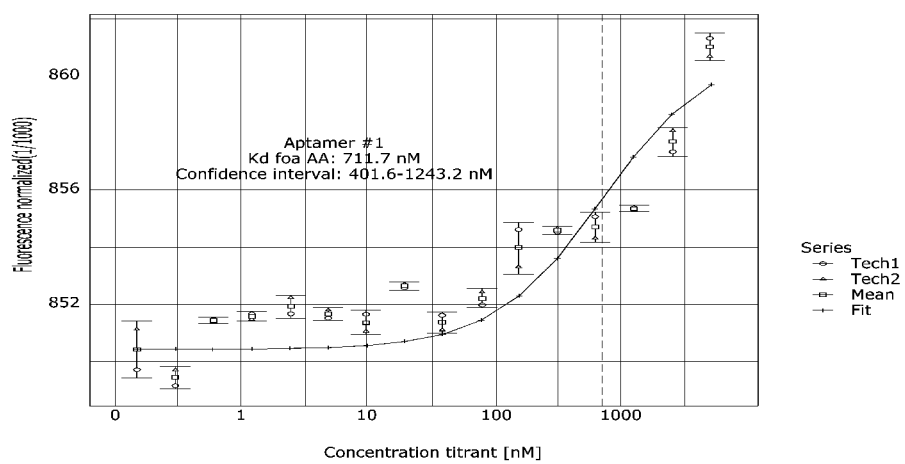
Figure 8:
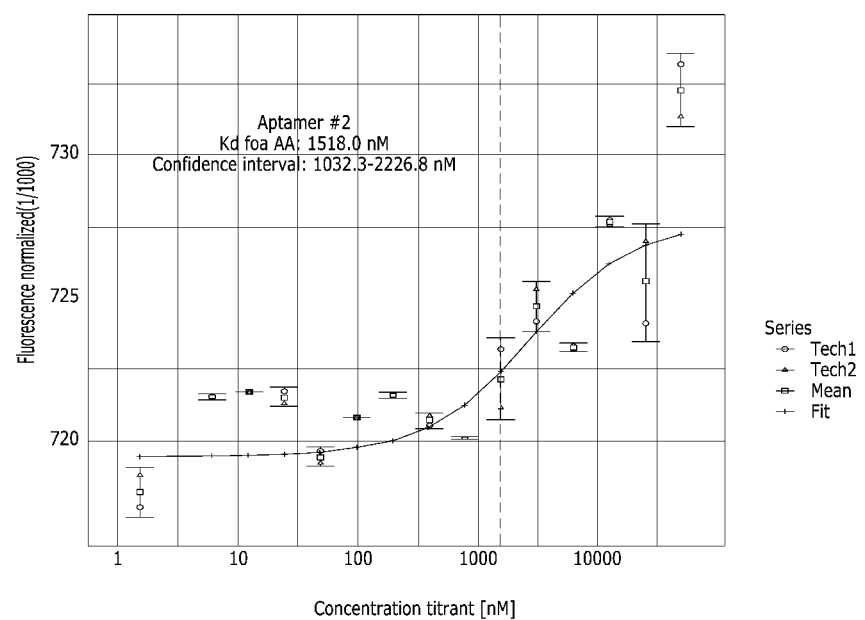
Figure 9:
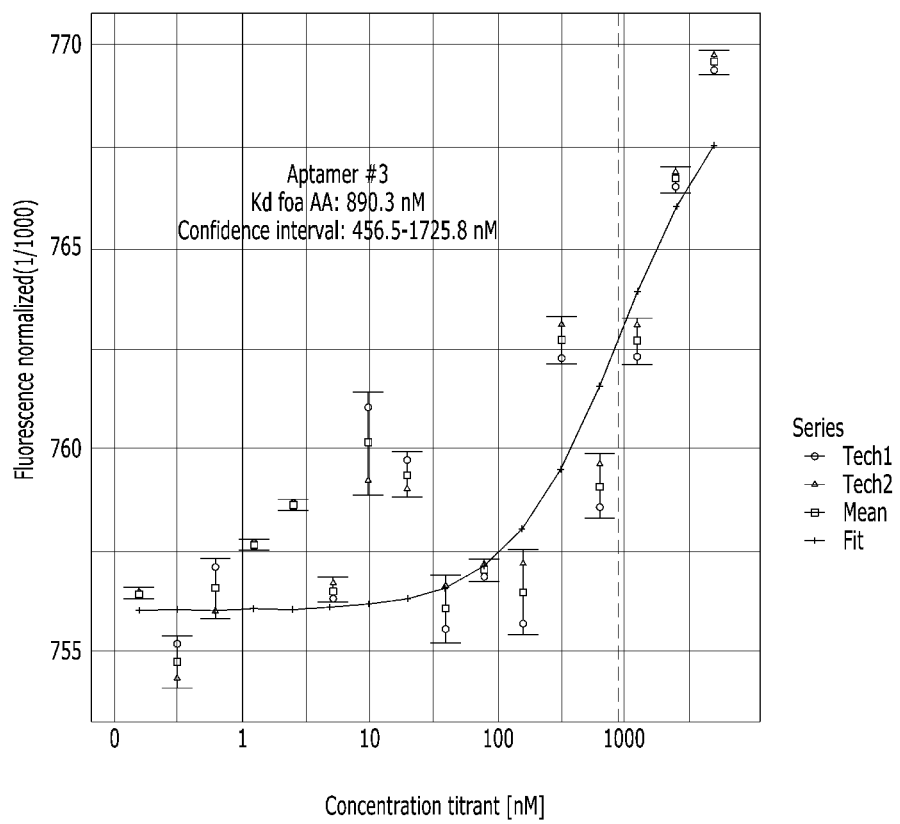
Figure 10:
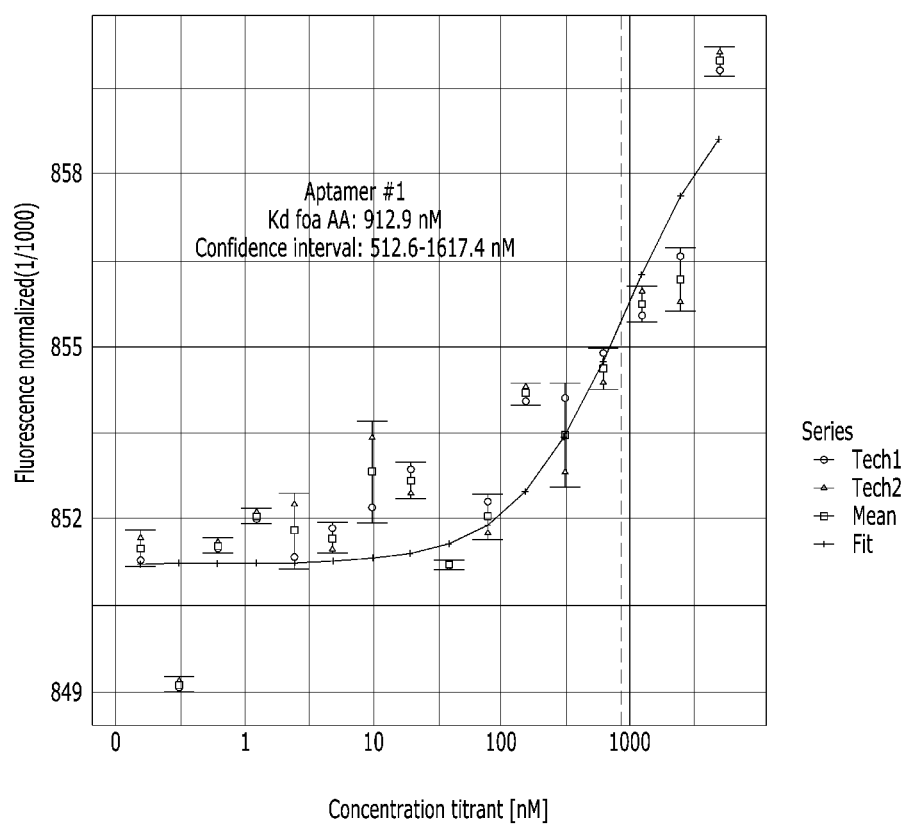
Figure 11:
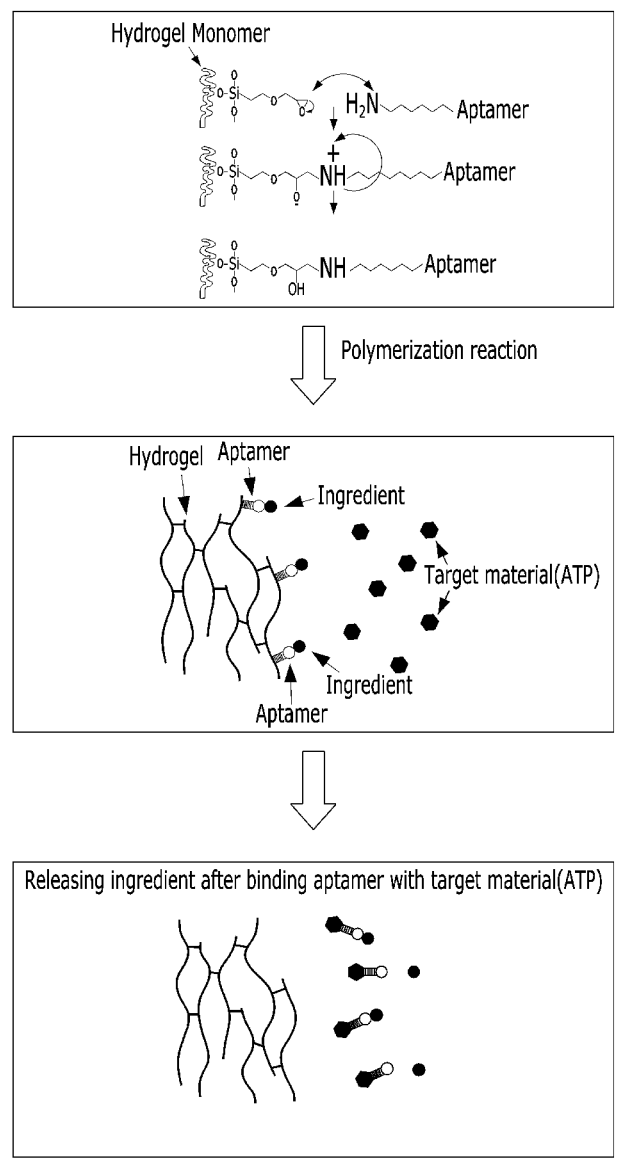
FIGS. 11 and 12 illustrate a method of producing a functional smart hydrogel using an aptamer of the present disclosure.
Figure 12:
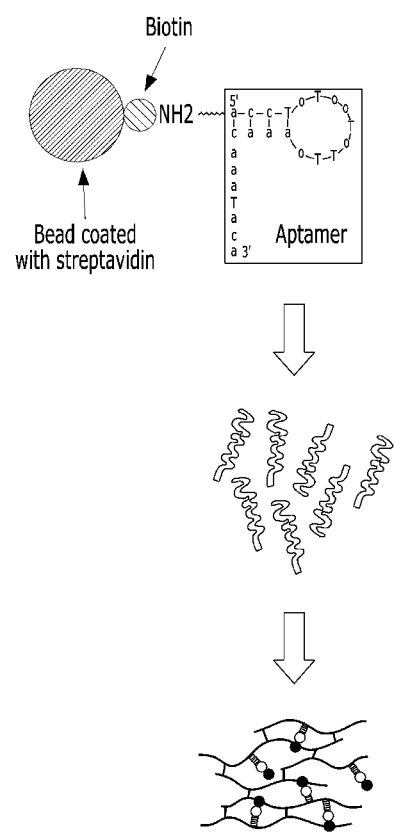
Figure 13:
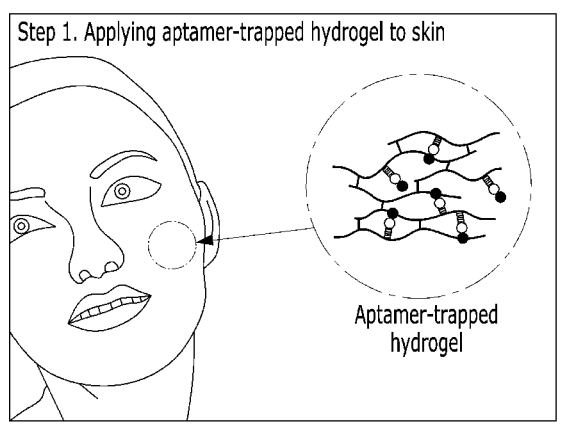
FIGS. 13 to 15 illustrate a process for aptasensing of a hydrogel in which an aptamer of the present disclosure is trapped.
Figure 14:
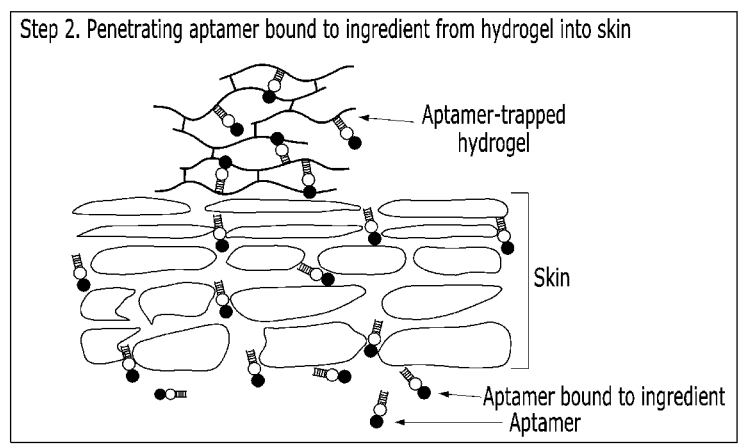
Figure 15:
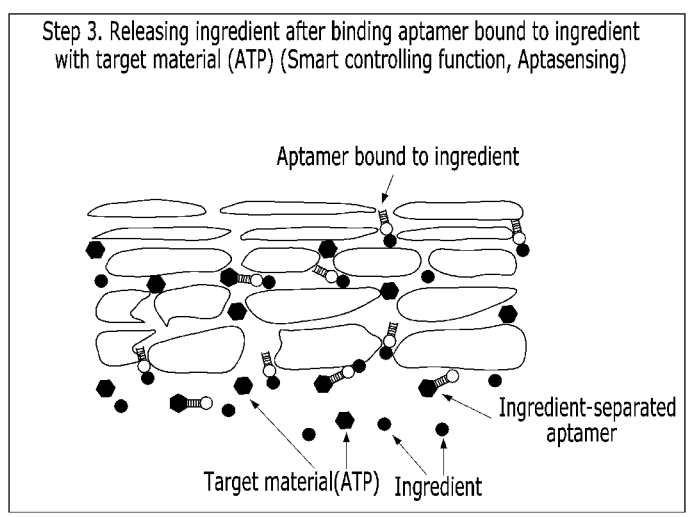

All three aptamers among them prevented oxidation of vitamin C by hydrogen peroxide. The #1, #2, and #3 aptamers, respectively, prevented oxidation of about 40%, about 20%, and about 40%. Based on these experiments and other experiences, it can be concluded that the three aptamers react directly to vitamin C and thus prevent oxidation of vitamin C (See FIGS. 2 to 4).

Example 3: Determination of Steady-State Solution Dissociation Constant (KD) of Aptamer of the Present Disclosure for Ascorbic Acid (AA) and Dehydroascorbic Acid (DHA)

The dissociation constants were determined using microscale thermophoresis (MST). The present Example includes MST data and KDs computed for the three aptamers in assay buffers for both targets. All reagents, including ascorbic acid and dehydroascorbic acid, were purchased from Sigma-Aldrich (St. Louis, Mo.), and deionized water was treated with Chelex-100 resin for 1 hour to remove accidental metals prior to buffer preparation. After Chelex treatment, the water was sprayed with nitrogen gas for 10 minutes to minimize oxygen and then kept sealed. This water was used in all aqueous solutions. The final buffer included 50 mM sodium acetate, pH 5.5, 1 mM $MgCl_2$, and 0.05% Tween-20. Both AA and DHA were analyzed in 1:1 passages dilution from e5 μM to 153 pM (final) (for aptamers #3 & #1) and from 50 μM to 1.53 nM (final) (for aptamer #2), respectively in buffer. The final concentration of each Cy5-conjugated aptamer is 20 nM. Each technical second dilution was measured twice on a Monolith NT.115 MST device from NanoTemper Technologies GmbH (Munich, Germany).

particles in the hydrogel by first attaching biotin to the amine group attached to the aptamer, then functionalizing them with the particle having streptavidin binding thereto, and then mixing them at a rate of 20% on calcination of the hydrogel. This method does not cause chemical bonding between the aptamer and the hydrogel, and it is relatively simple to implement.

Another method is to chemically attach the amine or carboxy group attached to the aptamer to the hydroxyl group of the hydrogel, which chemically binds the aptamer to the hydrogel.

In addition, various types of bonds can be brought by modifying the chemical composition of the hydrogel, or by changing the functional group to be bonded to the aptamer.

The specific trapping method includes the steps of a) binding the amine group to the aptamer, b) silanizing the hydroxyl group of the hydrogel monomer with 3-glycidoxypropyltrimethoxysilane (3-GPTMS) having an epoxy group, and then binding amine group binding to the aptamer to the epoxy group, and c) polymerizing the hydrogel monomer so that the aptamer-trapped hydrogel can be prepared.

Meanwhile, a collagen hydrogel, which is currently widely used due to moisturizing effects, can be made into an aptamer-collagen hydrogel in the same manner as described above, and it can add a function of more slowly releasing ingredients after sensing (detecting).

For example, a smart sensing (detecting) function can be added so that teprenone or caprylic acid, which is used to prevent skin aging, is gradually supplied to the skin with an aptamer-collagen hydrogel or is released according to the amount of cytokine related to skin aging, which is released from the cell.

SEQUENCE LISTING

```
<160> NUMBER OF SEQ ID NOS: 1

<210> SEQ ID NO 1
<211> LENGTH: 32
<212> TYPE: DNA
<213> ORGANISM: Artificial Sequence
<220> FEATURE:
<223> OTHER INFORMATION: aptamer

<400> SEQUENCE: 1
agagctcgcg ccggagttct caatgcaaga gc                                  32
```

The results are shown in FIGS. 5 to 10. Each data point is shown with a mean and fitted curve (black line) in the drawings. The vertical dashed line in each graph represents KD.

The following conclusions were deduced from the above results.

1) aptamers #3 and #1 have better selectivity for AA vs. DHA, while aptamer #2 has slightly better selectivity for DHA than AA.

2) aptamer #3 has the best selectivity for AA vs. DHA among the three aptamers.

3) aptamer #1 was the best for the protection of AA from oxidation but had the minimum selectivity for AA vs. DHA.

Example 4: Trapping of Aptamer on Hydrogel

The method of trapping the aptamer of the present disclosure on the hydrogel is a way to trap hydrothermal

What is claimed is:

1. A method of preventing oxidation of vitamin C by treating the vitamin C with an aptamer, wherein the aptamer includes a base sequence as set forth in SEQ ID NO:1.

2. A method for preparing an aptamer-trapped hydrogel, the method comprising the steps of:
   g) binding an amine group to the aptamer;
   h) silanizing a hydroxyl group of a hydrogel monomer with 3-glycidoxypropyltrimethoxysilane (3-GPTMS) having an epoxy group, and then binding an amine group binding to the aptamer to the epoxy group; and
   i) polymerizing the hydrogel monomer, wherein the aptamer includes a base sequence as set forth in SEQ ID NO:1.

* * * * *